United States Patent [19]

Bloom

[11] 4,067,872

[45] Jan. 10, 1978

[54] CYCLIC DERIVATIVES OF 1,2,3,4 TETRAHYDROQUINOLINE AND INDOLENE

[75] Inventor: Stanley M. Bloom, Waban, Mass.

[73] Assignee: Polaroid Corporation, Cambridge, Mass.

[21] Appl. No.: 721,857

[22] Filed: Sept. 9, 1976

Related U.S. Application Data

[63] Continuation-in-part of Ser. No. 592,396, July 2, 1975, abandoned, which is a continuation-in-part of Ser. No. 451,740, March 18, 1974, abandoned.

[51] Int. Cl.$^2$ .................. C07D 487/04; C07D 471/04
[52] U.S. Cl. .......................... 260/288 CF; 96/29 R; 96/66 HD; 96/66 R; 96/76 R; 96/95; 260/283 CN; 260/287 T; 548/359
[58] Field of Search ......... 260/288 CF, 310 A, 310 D

[56] References Cited

U.S. PATENT DOCUMENTS

| | | | |
|---|---|---|---|
| 2,421,693 | 6/1947 | Harriman | 260/288 CF |
| 3,407,206 | 10/1968 | Bousquet | 260/310 D |
| 3,454,579 | 7/1969 | Wright | 260/287 CF |
| 3,634,426 | 1/1972 | Eberle | 260/310 D |
| 3,652,570 | 3/1972 | Gettos et al. | 260/288 CF |
| 3,655,648 | 4/1972 | Houlihan et al. | 260/287 CF |
| 3,770,447 | 11/1973 | Bore et al. | 260/310 A |

OTHER PUBLICATIONS

Alley et al., Chem. Abs. vol. 53:11349h, (1959).
Hunt et al., Chem. Abs. vol. 77: 101495k (1972).

*Primary Examiner*—Paul M. Coughlan, Jr.
*Assistant Examiner*—Mary C. Vaughn
*Attorney, Agent, or Firm*—Sybil A. Campbell

[57] ABSTRACT

In one embodiment, the present invention relates to novel heterocyclic compounds as represented in the following formula

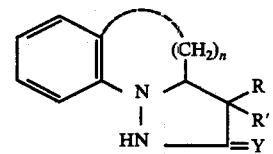

wherein R and R' each are hydrogen or alkyl, Y is =O or =NH and $n$ is a positive integer from 1 to 7.

In another embodiment, the present invention is directed to the use of the above-denoted class of heterocyclic compounds as photographic silver halide developing agents and to photographic processes, products and compositions employing the same.

11 Claims, 1 Drawing Figure

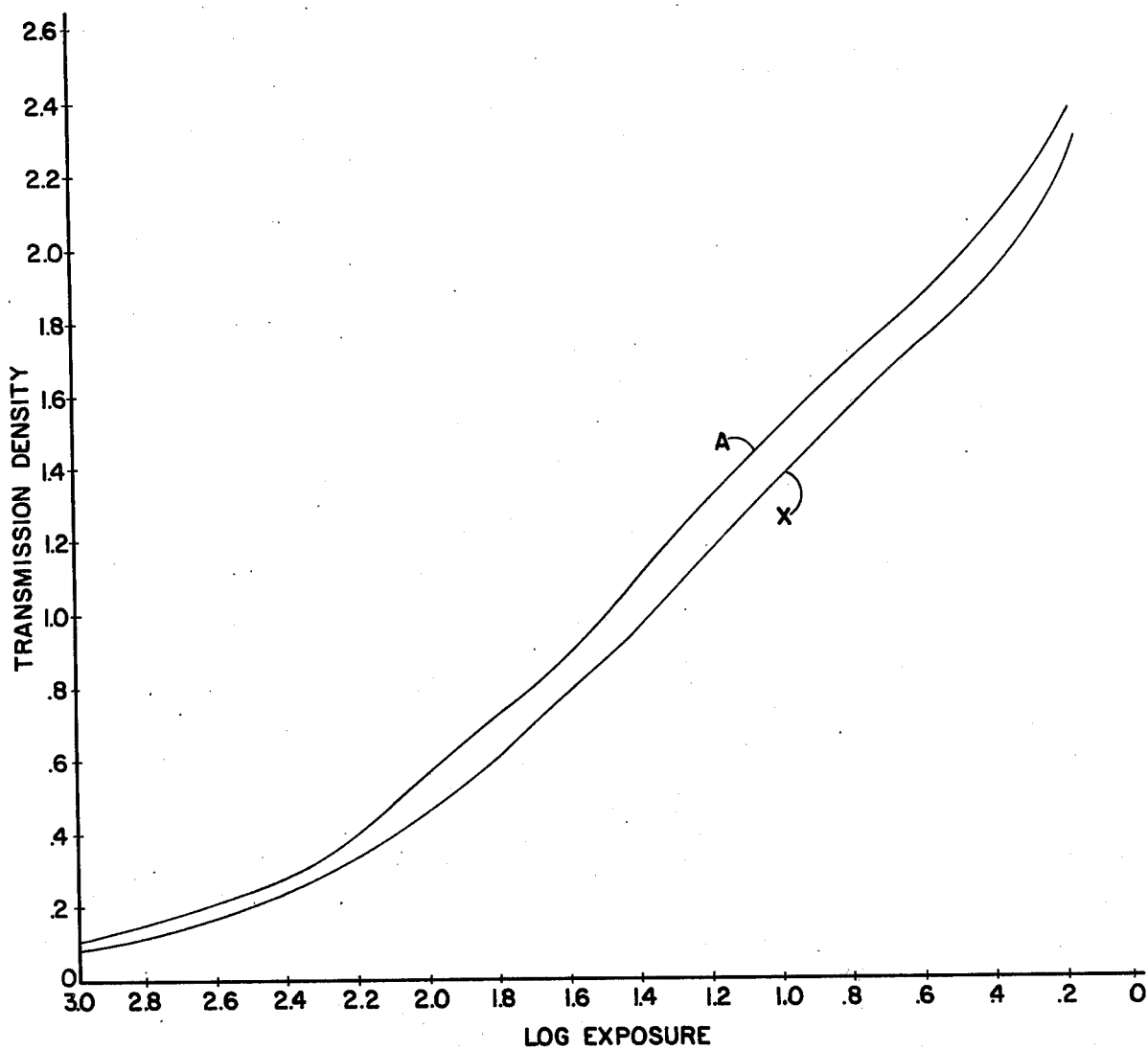

CYCLIC DERIVATIVES OF 1,2,3,4 TETRAHYDROQUINOLINE AND INDOLENE

CROSS-REFERENCE TO RELATED PATENT APPLICATIONS

This application is a continuation-in-part of U.S. patent application Ser. No. 592,396 filed July 2, 1975, now abandoned, which, in turn, is a continuation-in-part of U.S. patent application Ser. No. 451,740 filed Mar. 18, 1974, now abandoned.

BACKGROUND OF THE INVENTION

1. Field of the Invention

This invention relates to photography and to novel chemical compounds useful therein. More particularly, it relates to novel chemical compounds useful in the development of photosensitive silver halide materials and to photographic products, processes and compositions employing the same.

2. Description of the Prior Art

In recent years, there has been a growing interest in heterocyclic developing agents, i.e., developers containing a heterocyclic ring as part of their structure. Some of these developing agents have the conventional hydroxyl or amino developing groups substituted on adjacent carbon atoms of a heterocyclic ring to provide structures similar to those of the developing agents in the aliphatic and aromatic series. Still other heterocyclic developing agents, as exemplified by 1-phenyl-3-pyrazolidinimine and 1-phenyl-3-pyrazolidone (commercially available under the trademark "Phenidone") have one of the functional developing groups included as part of the heterocyclic ring. 1-phenyl-3-pyrazolidinimine forms the subject matter of British patent specification No. 757,840 and 1-phenyl-3-pyrazolidone and its 4,4-dialkyl derivatives form the subject matter of U.S. Pat. Nos. 2,289,367 and 2,772,282, respectively. Though these developing agents are useful by themselves, their commercial significance resides primarily in their ability to form superadditive mixtures with other developing agents, for example, hydroquinones.

The present invention is concerned with novel heterocyclic compounds comprising a new class of silver halide developing agents useful in conventional and in diffusion transfer photography, both black-and-white and color.

SUMMARY OF THE INVENTION

It is, therefore, one object of the present invention to provide novel heterocyclic compounds.

Another object of the present invention is to provide photographic products, processes and compositions employing the subject compounds for development of photosensitive silver halide materials.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description taken in connection with the accompanying drawing.

BRIEF DESCRIPTION OF THE DRAWING

The accompanying FIGURE is a transmission density-log exposure plot comparing the characteristic curves (H and D curves) of negative images obtained by development of a photosensitive material with (a) 1-phenyl-3-pyrazolidone ("Phenidone") in combination with hydroquinone and with (b) a developing agent of the present invention also in combination with hydroquinone.

DETAILED DESCRIPTION OF THE INVENTION

According to the present invention, it has been found that the novel heterocyclic compounds as represented in formula I below are useful as photographic silver halide developing agents and may be used alone or in combination with polyhydroxybenzenes, aminophenols and other developing agents. Indeed, it has been found that the heterocyclic compounds of the present invention as compared to other heterocyclic developing agents, such as 1-phenyl-3-pyrazolidone, provide an increase in film speed in conventional and in diffusion transfer photography when employed in combination with other developing agents, such as, hydroquinone. Moreover, the subject compounds have a colorless oxidation product which renders them especially useful as developing agents in diffusion transfer processes where the negative and positive elements are retained as an integral unit subsequent to processing and in the production of silver transfer images where it is inconvenient or undesired to wash the silver transfer image after separation of the negative and positive elements.

The novel compounds of the present invention which comprise this new class of heterocyclic photographic developing agents may be represented by the formula:

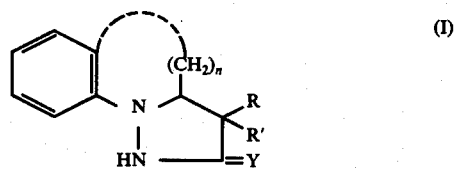

(I)

wherein R and R' each are hydrogen or lower alkyl having 1 to 4 carbon atoms, Y is =O or =NH and n is a positive integer from 1 to 7 and preferably 1 or 2. In a preferred embodiment, R and R' both are lower alkyl and usually are the same, for example, methyl. The preferred compounds comprise a particularly useful group of developing agents for both conventional and diffusion transfer photography due to the alkali stability of the ion-radical intermediate, a property believed to result from the planarity of the molecule.

The developing agents of the present invention may be prepared from certain substituted N-heterocyclic compounds as represented in formula II below by nitrosation of the selected starting material to form the corresponding N-nitroso intermediate followed by ring closing to yield the developing agent product. The N-heterocyclic starting materials may be represented by the formula

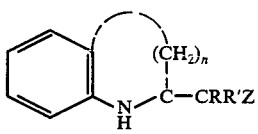

(II)

wherein Z is —CN or —COOR″ wherein R″ is alkyl, usually lower alkyl having 1 to 4 carbon atoms and R,R′ and n have the same meaning given in formula I above. Where Y is =O in the developing agent product, the starting material is an alkanoic acid ester, i.e., Z is —COOR″, and where Y is =NH in the developing agent product, the starting material is an alkyl nitrile, i.e., is —CN.

The aforementioned N-nitroso intermediates may be represented by the formula

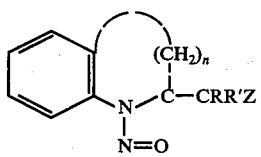

(III)

wherein R, R′, n and Z have the same meaning given in formula II. These intermediates form the subject matter of copending U.S. patent application Ser. No. 721,858 of James R. Bartels-Keith et al. filed concurrently herewith which, in turn, is a continuation-in-part of U.S. patent application Ser. No. 592,397 filed July 2, 1975, now abandoned.

The acid ester and nitrile starting materials are known and may be prepared in a conventional manner. For example, acid esters, such as, ethyl 1,2,3,4-tetrahydro-2-quinolylacetate and nitriles, such as, 1,2,3,4-tetrahydro-2-quinolylacetonitrile may be synthesized according to the procedures reported by G. Jones and J. Wood, Tetrahedron, Vol. 21, pp. 2951–2971 (1965). The indoline esters and nitriles may be prepared, for example, by reduction of the corresponding indoles. In preparing the N-nitroso intermdiates, an aqueous solution of sodium nitrite is added to a solution of the selected starting material in dilute aqueous hydrochloric acid at room temperature. Depending upon the particular nitroso compound, ring-closing to the developing agent product may be achieved by reduction alone or by reduction followed by cyclization. For example, ring-closing of the N-nitroso quinoline compounds may be carried out by treating the N-nitroso compounds with zinc dust in a solvent, such as dilute glacial acetic acid, while maintaining the temperature between about 10° and 20° C. The reaction mixture is then stirred at room temperature, the zinc dust removed by filtration and the developing agent product isolated from the filtrate. Ring-closing of the N-nitroso indoline compounds may be carried out by electrolytic reduction followed by heating in quinoline.

The following examples illustrate the preparation of compounds within the scope of this invention and are given for purposes of illustration only.

COMPOUND A

Preparation of

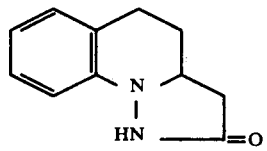

1. A colorless solution of 16 gms. of ethyl 1,2,3,4-tetrahydro-2-quinolylacetate in 150 mls. of 10% hydrochloric acid was stirred at room temperature, and 5 gms. of sodium nitrite in 30 mls. of water were added dropwise over a period of about 20 minutes. No heat was evolved. After addition was complete, stirring was continued for another 20 minutes. The solution turned orange, and a dark orange oil precipitated. The orange oil was taken up in benzene, and the benzene solution was washed to neutral, dried and stripped. The dark orange oil was then taken up in hexane, and after boiling, the solution was decanted from the brown insoluble residue. The hexane solution was then cooled in an ice bath and decanted from the yellow-brown oil that formed. The decanted solution was stripped leaving 14 gms. of a yellow oil comprising the corresponding N-nitroso compound having the formula

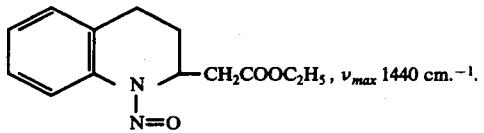

2. Ethyl 1-nitroso-1,2,3,4-tetrahydro-2-quinolylacetate obtained in step 1 (14 gms.) was dissolved in dilute acetic acid (60 mls. water:80 mls. glacial acetic acid). The resulting solution was stirred at 16° C. in an ice bath under nitrogen, and 5 gms. of zinc dust were added in three portions. After the first addition, the temperature rose to 20° C. and the mixture was stirred in the ice bath for about 20 minutes until the temperature was about 16° C. The second portion was added, and the temperature rose to about 18° C. after which stirring in the ice bath was continued for another 15 minutes. After the third addition, the temperature rose from 13° to 17° C. The mixture was then removed from the ice bath and stirred at room temperature for about 30 minutes at which time the temperature was about 25° C.

The zinc was removed from the mixture by filtering through a sintered funnel. The filtrate was stripped at 55° C. leaving a gummy crystalline residue that was refrigerated overnight. The residue was taken up in chloroform/water, and the solvent was washed well, dried and stripped at 38° C. leaving a yellow oil (13.5 gms.). The oil was taken up in a mixture of hexane and benzene and the title compound was recovered as white crystals from the solvent mixture by filtering and drying in vacuuo over $P_2O_5$ at room temperature, melting range 196°–197° C.

COMPOUND B

Preparation of

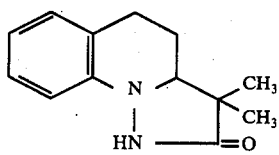

Step (1) of the foregoing procedure used in the preparation of Compound A was repeated using as the acid ester starting material, the compound

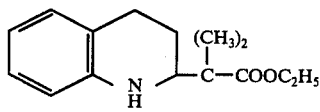

(1.3 gms) in 15 mls. of 15% hydrochloric acid and 1 gm. of sodium nitrite in 5 mls. of water to give the corresponding N-nitroso intermediate as a yellow oil having the formula

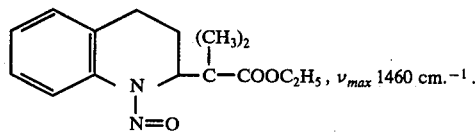

2. The nitroso compound prepared above (1 gm) was dissolved in dilute acetic acid (8 mls. water: 11 mls. glacial acetic acid) in a water bath at a temperature of about 22° C. Zinc dust (1 gm) was added in portions to maintain the temperature at about 31°–32° C. After the addition was complete, the reaction mixture was heated at about 55° C. for 1 hour and then at 75° C. for about one-half hour. The reaction mixture was cooled, filtered to remove the zinc and stripped leaving a gummy solid. The solid was taken up in chloroform/water, and the solvent layer washed to neutral, dried and stripped to a brown oil. Crystallization of the oil from hexane/benzene gave a brown flocculant solid which was removed by filtration. Upon cooling and scratching, off-white crystals formed in the filtrate which were collected by filtration and chromatographed on silica gel using benzene, benzene/5% ether, benzene/10% ether and benzene/25% ether. The oil eluted with benzene/10% ether crystallized and the solid obtained was recrystallized to give the title compound as off-white crystals (melting range 148°–150° C.).

COMPOUND C

Preparation of

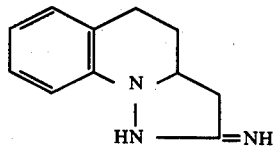

1. A solution of 9.7 gms. of 1,2,3,4-tetrahydro-2-quinolylacetonitrile in 200 mls. of 10% hydrochloric acid was stirred at room temperature, and 5 gms. of sodium nitrite in 25 mls. of water were added slowly. The resulting solution became a reddish color and then a red-brown oil precipitated. The solution was allowed to stand for about 4 days. The red-brown oil was extracted into benzene, and the benzene solution washed and dried and then stripped to leave about 8 gms. of brown oil. The aqueous reaction solution was made basic and again extracted with benzene to give an additional gram of brown oil. The oils were combined and chromatographed on Florisil using benzene as the eluent. About 3 gms. of oil were collected comprising the corresponding N-nitroso compound having the formula

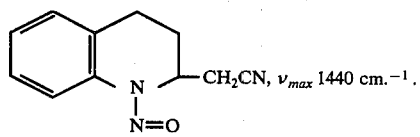

2. 1-nitroso-1,2,3,4-tetrahydro-2-quinolylacetonitrile obtained in step 1 (3 gms.) was dissolved in 20 mls. of glacial acetic acid and this solution added dropwise to a mixture of zinc dust in 20 mls. of water cooled to 15° C. and stirred under nitrogen. Addition was conducted at a rate to keep the temperature at about 15°–16° C. and the nitrile solution washed in with 5 mls. of glacial acetic acid. The reaction mixture was stirred in an ice bath for about one-half hour and then allowed to come to room temperature.

The zinc removed by filtering through a sintered funnel under nitrogen. The filtrate was stripped under vacuum at about 40° C. to leave a solid that was taken up in chloroform/water under nitrogen. The water layer was pink—then blue—then colorless. The solvent layer was dried and stripped leaving a gummy white crystalline solid. A mixture of chloroform/benzene/hexane was added to the white crystalline solid and a gray solid crystallized which was dried in vacuo at room temperature. The gray solid was dissolved in benzene and the benzene solution filtered through a sintered funnel to remove remaining zinc. Shiny white plates slowly crystallized in the filtrate upon standing. The white plates were dried under vacuum at room temperature to give 1.0 + gms. of the title compound (melting range 152°–154° C.).

COMPOUND D

Preparation of

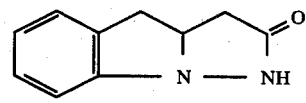

1. To a 3.3 gm sample (0.016M) of ethyl-2-indolinylacetate was added 40 cc. of 10% hydrochloric acid and the mixture cooled to 10°–20° C. while stirring. A solution of 3.5 gms of sodium nitrite (0.05M) in 20 cc. of water was added dropwise. Then the mixture was allowed to stir at 10°–20° C. for 1 hour. The reaction product was extracted into benzene and the benzene layer washed with a little sodium bicarbonate solution. After drying, over sodium sulfate, the benzene solution was filtered and the solvent evaporated on a rotary evaporator. The corresponding N-nitroso compound having the following formula was obtained as a brown oily solid.

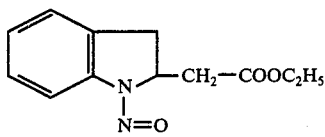

2. Ethyl 2-(N-nitrosoindolinyl) acetate (0.015–0.025 mole) was dissolved in 400 ml of a 50/50 mixture of 0.10M phosphate buffer and absolute ethanol. The dark solution was transferred to the cathode compartment of a water-jacketed electrolysis cell. Phosphate-ethanol mixture (60 ml) and 4N hydrochloric acid (5 ml) were added to the anode compartment. The solution was degassed for 15 minutes with nitrogen followed by the adjustment of pH of the cathode compartment to approximately 4.0 with 4N HCl. The reduction occurred at a mercury cathode (constant potential, 1.200 volts vs. saturated calomel electrode). A rotating platinum electrode was used as the anode. Initially the current ranged from 200–300 ma and after about 15–20 hours had decreased to 15–20 ma. The reduction of substrate was monitored by polarographic analysis and a digital coulometer, the latter revealing a four electron process. In concluding the electrolysis the light yellow solution was transferred from the electrolysis cell, and the ethanol was evaporated. The aqueous mixture was extracted with chloroform, dried over anhydrous MgSO$_4$ and evaporated to give the hydrazine as a dark oil in 90–95% yield. The free base was converted to the hydrochloride salt with absolute ethanol saturated with HCl gas at 0° C. The salt was filtered and recrystallized from ethanol-ether to give a pale yellow solid, (m.p. 153°–155°). Reaction of the hydrazine salt with acetone gave the corresponding Schiff base, m.p. 157°–158°.

3. The reduced compound (0.656 mmole) in CDCl$_3$ was placed in a pear-shaped flask and the CDCl$_3$ removed in vacuo. Quinoline (redistilled; 12.692 mmole) and a micro-stirrer bar were added and the air removed by blowing a stream of nitrogen over the mixture for some time. Meanwhile an oil bath was preheated to 190°–195° C. Then the mixture was placed in the bath, stirred under nitrogen at 187°–195° C. (mostly around 193° C.) for 10 minutes, then removed and allowed to cool under nitrogen. As much quinoline as possible was distilled off in vacuo (bath temperature approximately 90° C., 0.27 mm) and the residue kept overnight under nitrogen. The mixture was shaken with saturated aqueous potassium bicarbonate to neutralize any hydrochlorides and then extracted with chloroform (4 ml and 2 × 1 ml). The dried chloroform extracts were washed once with saturated aqueous potassium bicarbonate (about 4 ml), dried with magnesium sulfate and evaporated first in a stream of nitrogen to remove chloroform and then in vacuo (bath temperature about 90° C., 0.27 mm) to remove as much quinoline as possible. The resulting dark brown gum comprising the title compound was taken up in CDCl$_3$ (0.9 ml) freed from traces of magnesium sulfate and after running a $^{13}$C nmr spectrum which confirmed the presence of the title compound, the compound was recovered by evaporation in a stream of nitrogen, mixing the partly crystallized residue with ether and then removing the ether (filterstick). The treatment with ether was repeated three times to remove as much quinoline as possible. To the residue was added chloroform (about 1 ml) and the mixture cooled to −60° C. and the chloroform removed. To the residual crystals was added chloroform, the mixture cooled again and the operation repeated. The crystalline residue (somewhat discolored prisms) was dried in vacuo leaving the title compound having a melting range of 150°–153.5° C.

To illustrate its usefulness as a reducing agent for silver halide, a few crystals of the title compound were placed on Velox paper (a photographic printing paper containing a silver chloride emulsion), and a few drops of 1N aqueous sodium hydroxide was placed on the crystals to dissolve them. The silver salt in the area of the dissolved crystals was reduced as evidenced by the appearance of a dark spot. No darkening occurred with the 1N sodium hydroxide alone.

The ethyl-2-indolinylacetate used in the above example was prepared as follows:

a. 22.2 gm (0.17M) of ethylacetoacetate was added dropwise to a well-stirred suspension of 7.6 gm (0.18M) of sodium hydride, (57% in mineral oil) in 300 ml of dry benzene, keeping the mixture in a nitrogen atmosphere. The reaction mixture was stirred for 1 hour under nitrogen. 33.9 gm of o-nitrophenylacetylchloride in 100 cc. dry benzene was added dropwise over a period of approximately 45 minutes. The mixture was allowed to stir for 1 hour at room temperature. The mixture was then diluted with 150 cc. dry benzene and washed twice with 150 cc. water. The benzene layer was dried over anhydrous sodium sulfate. (Additional product can be obtained by acidifying the water layer and extracting with ethyl ether). The solvent was removed and the ethyl-o-nitrophenylacetylacetoacetate product was crystallized by treatment with methanol and recovered as a pale colored material.

b. 30 gm (0.103M) ethyl-o-nitrophenylacetylacetoacetate was added over a period of 15–20 minutes to a saturated ammoniacal ethanol solution (prepared by bubbling NH$_3$ gas into 400 cc. absolute alcohol for 15–20 minutes while cooling the solution to 0°–5° C.). The orangy mixture was stirred for 1 hour at 5°–10° C. and then left in the refrigerator overnight. The ethyl-γ-2-nitrophenylacetoacetate crystals formed were filtered and dried in vacuum. Additional solid was obtained after evaporation of the filtrate and washing with water to remove any amide formed.

c. A sample of 12.0 gm (0.048M) of ethyl-γ-2-nitrophenylacetoacetate was dissolved in 200 cc. glacial acetic acid. Approximately 2½ spatulas of 5% Pd/C was added to the solution and the compound was reduced on the Parr hydrogenator. Ethyl-2-indolylacetate was obtained as a dark orangy oily liquid after removal of catalyst and solvent.

d. 8.8 gm (0.04M) of the indole prepared in step (c) was dissolved in 150 cc. glacial acetic acid and cooled to ± 20° C. in an ice bath. 2.4 gm of sodium cyanoborohydride was added slowly over a period of 10–15 minutes. The mixture was allowed to stir at 20° C. for 1 hour and then poured into 150 cc. ice water. The product was extracted with ethyl ether and dried over anhydrous sodium sulfate. The ethyl ether was removed leaving ethyl-2-indolinylacetate as a dark oily material which was purified by extraction in petroleum ether/methanol and salt solution.

As indicated above, the novel compounds comprising the developing agents of the present invention while useful in conventional or "tray" development find particular utility in diffusion transfer processes for forming images in silver or in color. Such processes are now well known in the art; see for example, U.S. Pat. Nos.

2,543,181; 2,647,056; 2,983,606, etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving statum in superposed relationship with the silver halide emulsion to provide the desired transfer image.

In silver diffusion transfer processes, processing of the exposed silver halide emulsion is effected in the presence of a silver halide solvent, such as sodium thiosulfate, which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

In color diffusion transfer processes, a photosensitive component comprising at least one photosensitive silver halide emulsion having a dye image-providing compound associated therewith in the same or in an adjacent layer is exposed to form a developable image then developed with a processing composition to form an imagewise distribution of a soluble and diffusible image-providing material which is transferred, at least in part, by diffusion, to a superposed image-receiving component comprising at least a dyeable stratum. These processes rely for color image formation upon a differential in mobility or solubility of dye image-providing material obtained as a function of development so as to provide an imagewise distribution of such material which is more diffusible and which, therefore, may be selectively transferred to the superposed dyeable stratum. The differential in mobility or solubility may be obtained, for example, by a chemical action such as a redox reaction, a silver ion-assisted cleavage reaction or a coupling reaction.

The dye image-providing materials which may be employed in such processes generally may be characterized as either (1) initially soluble or diffusible in the processing composition but which are selectively rendered non-diffusible in an imagewise pattern as a function of development; or (2) initially insoluble or non-diffusible in the processing composition but which are selectively rendered diffusible in an image-wise pattern as a function of development. These materials may be complete dyes or dye intermediates, e.g., color couplers.

Examples of initially soluble or diffusible materials and their use in color diffusion transfer processes are disclosed, for example, in U.S. Pat. Nos. 2,647,049; 2,661,293; 2,698,244; 2,698,798; 2,802,735; 2,774,668; and 2,983,606. Examples of initially non-diffusible materials and their use in color transfer systems are disclosed in U.S. Pat. Nos. 3,443,939; 3,443,940; 3,227,550; 3,227,551; 3,227,552; 3,227,554; 3,243,294; 3,445,228; 3,719,488 and 3,719,489.

In any of these systems, multicolor images may be obtained by employing a photosensitive element containing at least two selectively sensitized silver halide layers each having associated therewith a dye image-providing material exhibiting the desired spectral absorption characteristics. The most commonly employed elements of this type are the so-called tripack structures employing a blue-, a green- and a red-sensitive silver halide layer having associated therewith, respectively, a yellow, a magenta and a cyan image-providing material.

The photosensitive and image-receiving elements may be separate components which are brought together during processing and thereafter retained together as the final print or separated following image formation; or they may together comprise a unitary structure, e.g., an integral negative-positive film structure wherein the negative and positive, i.e., the photosensitive element and image-receiving element are laminated and/or otherwise physically retained together at least prior to image formation. Integral negative-positive film structures adapted for forming color transfer images viewable without separation, i.e., wherein the image-receiving element containing the dye transfer image need not be separated from the photosensitive element for viewing purposes are described and claimed in U.S. Pat. Nos. 3,415,644; 3,415,645; 3,415,646; 3,573,943 and 3,573,044 in the name of Edwin H. Land and in U.S. Pat. Nos. 3,594,164 and 3,594,165 in the name of Howard G. Rogers.

In conventional development and in diffusion transfer photographic processes, the subject compounds may be used as the sole silver halide developing agent, or they may be employed in combination with another silver halide developing agent as an auxiliary developer or as the main component of the developing combination. Examples of developing agents that may be used in combination with the subject compounds include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as, 2,4,6-triaminophenol, 2,4-diaminophenol dihydrochloride and 4,6-diamino-ortho-cresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidine ascorbic acid; and hydroxylamines, such as, N,N-di-(2-ethoxyethyl)hydroxylamine and N,N-di-(2-methoxyethoxyethyl) hydroxylamine.

When the compounds of the present invention are used in diffusion transfer processes, the processing composition if it is to be applied to the emulsion by being spread thereon in a thin layer usually includes a film-forming thickening agent. The processing composition may comprise, for example, one or more developing agents of the present invention and optionally, one or more conventional developing agents such as those enumerated above, an alkali such as sodium hydroxide or potassium hydroxide and a film-forming thickening agent such as a high molecular weight polymer, e.g., sodium carboxymethyl cellulose or hydroxy ethyl cellulose. As noted above, in the production of silver transfer images, a silver halide solvent is employed which may be included in the processing composition, or if desired, a silver halide solvent precursor such as those disclosed in U.S. Pat. No. 3,698,898 of J. Michael Grasshoff and Lloyd D. Taylor may be disposed in a layer of the film unit. In addition to the above ingredients, the processing composition may be further modified by the inclusion of restrainers, preservatives and other components commonly employed in developer compositions. All these materials are preferably in aqueous solution.

Rather than being dissolved in the aqueous alkaline processing composition prior to application thereof to an exposed silver halide emulsion, the developing agents of the present invention may be disposed prior to exposure in the photosensitive element, e.g., by placing them in, or on behind a silver halide emulsion layer. In this instance, the processing composition containing the developing agent is formed by application to the photosensitive element of an aqueous alkaline solution capable of solubilizing the developing agent. In diffusion transfer processes, the subject developing agents usually are contained in the processing composition.

Because they do not give rise to oxidation products that stain the image, the developing agents of the present invention are especially useful in photographic processes wherein it is desired to eliminate or minimize the need for washing and stabilizing operations subsequent to the formation of the positive image, e.g., to eliminate the need for print coating silver transfer images. Since their oxidation products are non-staining, the subject developing agents also find utility in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in U.S. application Ser. No. 383,196 of Edwin H. Land filed July 27, 1973, now U.S. Pat. No. 3,894,871.

The following examples are given to illustrate the utility of the compounds of the present invention as photographic developing agents and are not intended to be limiting.

EXAMPLE I

Kodak Plus-X negative was exposed behind a step wedge and developed for 3½ minutes at a temperature of 21° C. in a developer having the following composition and was then fixed and washed:

| Water | 750.0 cc. |
|---|---|
| Sodium Sulfite | 75.0 g. |
| Sodium Carbonate | 37.5 g. |
| Potassium Bromide | 2.0 g. |
| Benzotriazole | 0.15 g. |
| Hydroquinone | 8.0 g. |
| Compound A | 0.25 g. |
| Water to 1 liter | |

For comparative purposes, the above procedure was repeated except that a molecular equivalent, 0.21 g. of 1-phenyl-3-pyrazolidone ("Phenidone") was substituted for Compound A in the developer composition.

The sensitometric data obtained from the processed negatives are plotted as D log E curves in the accompanying FIGURE. In the FIGURE, the curve designated A represents the results obtained using Compound A as a booster developer with hydroquinone, and the curve designated X represents the results obtained in the control using "Phenidone" as the booster developer.

As will be evident from reference to the characteristic, curves, an increase in effective film speed was obtained with the compound of the present invention. Numerically expressed, the difference in film speed between curves A and X was $\Delta = 0.14$, which is equivalent to approximately ½ stop increased film speed by use of the developer of the present invention.

EXAMPLE II

A Polaroid Land Type 105 negative comprising a photosensitive silver halide emulsion was exposed in an automatic recording densitometer and processed by spreading a layer of processing composition approximately 0.0016 inch thick between the exposed emulsion and a superposed Polaroid Land Type 107 image-receiving element. The processing composition employed was prepared by adding 0.35 gm. of Compound A to 10 cc. of the following formulation:

| Water | 40 cc. |
|---|---|
| Potassium Hydroxide (Aqueous 45% w/w solution) | 6.6 gm. |
| Potassium thiosulfate | 1.0 gm. |
| Sodium carboxymethyl cellulose | 2.0 gm. |

After an imbibition time of approximately 1 minute, the negative was stripped from the image-receiving element. The maximum and minimum reflection densities measured for the positive image were 1.0 and 0.12, respectively.

In a comparative example, the procedure of Example II was repeated except that a molecular equivalent (0.3 gm./10cc.) of 1-phenyl-3-pyrazolidone ("Phenidone") was used as the developing agent instead of Compound A. The positive image obtained showed substantially less density as evidenced by maximum and minimum reflection densities of 0.4 and 0.03, respectively.

It will be apparent that the relative proportions of the subject developing agents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the developer compositions, other components as commonly used in the photographic art.

Since certain changes may be made in the above compositions and processes without departing from the scope of the invention herein involved, it is intended that all matter contained in the above description should be interpreted as illustrative and not in a limiting sense.

What is claimed is:

1. A compound of the formula:

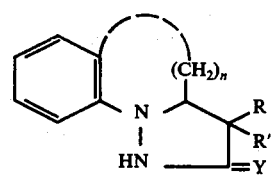

wherein R and R' each are hydrogen or lower alkyl having 1 to 4 carbon atoms, Y is =O or =NH and $n$ is a positive integer 1 or 2.

2. A compound of the formula

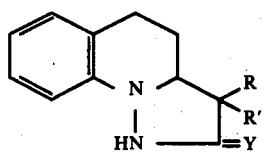

wherein R and R' each are hydrogen or lower alkyl having 1 to 4 carbon atoms and Y is =O or =NH.

3. A compound as defined in claim 1 wherein said R and R' are hydrogen.

4. A compound as defined in claim 1 wherein said R and R' are lower alkyl.

5. A compound as defined in claim 1 wherein said *n* is 1.

6. A compound as defined in claim 1 wherein Y is =O.

7. A compound as defined in claim 1 wherein Y is =NH.

8. The compound having the formula:

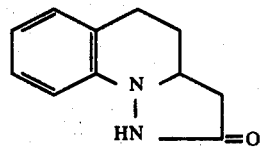

9. The compound having the formula:

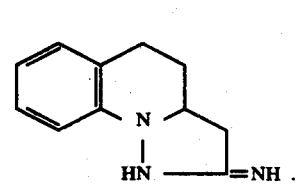

10. The compound having the formula:

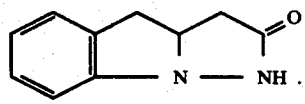

11. The compound having the formula:

* * * * *